(12) United States Patent
Tarunaga et al.

(10) Patent No.: US 10,980,987 B2
(45) Date of Patent: Apr. 20, 2021

(54) BALLOON CATHETER AND METHOD OF MANUFACTURING LONG MEMBER FOR BALLOON CATHETER

(71) Applicant: TERUMO KABUSHIKI KAISHA, Tokyo (JP)

(72) Inventors: Akihiko Tarunaga, Shizuoka (JP); Kenta Suzuki, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 251 days.

(21) Appl. No.: 15/940,336

(22) Filed: Mar. 29, 2018

(65) Prior Publication Data
US 2018/0214677 A1 Aug. 2, 2018

Related U.S. Application Data

(63) Continuation of application No. PCT/JP2016/078509, filed on Sep. 27, 2016.

(30) Foreign Application Priority Data

Sep. 29, 2015 (JP) .............................. JP2015-190974

(51) Int. Cl.
*A61M 25/10* (2013.01)
*A61M 25/00* (2006.01)
*A61M 25/01* (2006.01)

(52) U.S. Cl.
CPC .... *A61M 25/1036* (2013.01); *A61M 25/0009* (2013.01); *A61M 25/0028* (2013.01);
(Continued)

(58) Field of Classification Search
CPC .. A61M 2025/0034; A61M 2025/0183; A61M 2025/1056; A61M 25/0009;
(Continued)

(56) References Cited

U.S. PATENT DOCUMENTS 5,188,596 A * 2/1993 Condon ............. A61B 1/00082
600/116
5,411,016 A * 5/1995 Kume ................ A61B 1/00082
600/114
(Continued)

FOREIGN PATENT DOCUMENTS

JP 2001-191412 A 7/2001
JP 2007-503869 A 3/2007
(Continued)

OTHER PUBLICATIONS

English translations of PCT Written Opinion of the International Searching Authority and International Search Report dated Jan. 31, 2017 (Japanese language submitted with the IDS filed Mar. 29, 2018).

(Continued)

*Primary Examiner* — Mohamed G Gabr
(74) *Attorney, Agent, or Firm* — Buchanan Ingersoll & Rooney PC

(57) ABSTRACT

A balloon catheter is disclosed, which is capable of improving accuracy of an inspection result of a tube wall of an elongated member constituting a catheter shaft and achieving further improved product quality through the inspection, and a method of manufacturing an elongated member for a balloon catheter, which is used for the balloon catheter. In an outer tube of a balloon catheter, distal from a proximal end of a guide wire lumen is formed of a transparent material. From a distal end toward a proximal end, an inner tube of the balloon catheter has at least a first region and a second region, the second region being a transparent region that is more transparent than the first region.

15 Claims, 7 Drawing Sheets

(52) U.S. Cl.
CPC ........ *A61M 25/0043* (2013.01); *A61M 25/10* (2013.01); *A61M 25/1034* (2013.01); *A61M 2025/0034* (2013.01); *A61M 2025/0183* (2013.01); *A61M 2025/1056* (2013.01)

(58) Field of Classification Search
CPC .......... A61M 25/0028; A61M 25/0043; A61M 25/10; A61M 25/1034; A61M 25/1036; A61B 1/00082; A61B 1/00154; A61B 2017/22051; A61B 2090/3966; A61B 90/361; A61B 17/22
See application file for complete search history.

(56) References Cited

U.S. PATENT DOCUMENTS

| | | | | |
|---|---|---|---|---|
| 6,942,648 | B2* | 9/2005 | Schaible | A61M 25/00 604/264 |
| 2005/0049552 | A1 | 3/2005 | Holzapfel et al. | |
| 2012/0253114 | A1* | 10/2012 | Kinoshita | A61B 1/00154 600/104 |
| 2012/0296364 | A1 | 11/2012 | Gundale et al. | |
| 2013/0217964 | A1* | 8/2013 | Kumoyama | A61B 1/00082 600/104 |

FOREIGN PATENT DOCUMENTS

| | | |
|---|---|---|
| JP | 2014-195487 A | 10/2014 |
| WO | WO 2012/042619 A1 | 4/2012 |
| WO | WO 2014/156600 A1 | 10/2014 |

OTHER PUBLICATIONS

International Search Report (PCT/ISA/210) dated Jan. 31, 2017, by the Japanese Patent Office as the International Searching Authority for International Application No. PCT/JP2016/078509.

Written Opinion (PCT/ISA/237) dated Jan. 31, 2017, by the Japanese Patent Office as the International Searching Authority for International Application No. PCT/JP2016/078509.

Notice of Reasons for Refusal issued by the Japanese Patent Office in corresponding Japanese Patent Application No. 2020-054843 dated Jan. 5, 2021 (8 pages including partial English translation).

* cited by examiner

BALLOON CATHETER AND METHOD OF MANUFACTURING LONG MEMBER FOR BALLOON CATHETER

CROSS-REFERENCES TO RELATED APPLICATIONS

This application is a continuation of International Application No. PCT/JP2016/078509 filed on Sep. 27, 2016, which claims priority to Japanese Application No. 2015-190974 filed on Sep. 29, 2015, the entire contents of both of which are incorporated herein by reference.

TECHNICAL FIELD

The present disclosure generally relates to a balloon catheter serving as a medical device, and a manufacturing method of an elongated member for a balloon catheter.

BACKGROUND DISCUSSION

A balloon catheter is known as a medical device used in performing a medical procedure for widening a lesion area (stenosed site) formed in a living body lumen such as a blood vessel, or used in causing a stent to indwell the lesion area.

As the balloon catheter, an over-the-wire type and a rapid exchange type are generally known.

The balloon catheter of the rapid exchange type is configured so that a guide wire is inserted into only a distal portion side of an elongated member called a catheter shaft having a balloon located therein.

Therefore, a guide wire port (opening portion) through which the guide wire is inserted into or removed from the catheter shaft is disposed in an intermediate portion in an axial direction of the catheter shaft.

As a manufacturing method of the catheter shaft used for the balloon catheter of the rapid exchange type, for example, a method disclosed in JP-A-2014-195487 has been proposed.

According to this manufacturing method, a thermal fusion process is performed in which a distal side shaft, an inner tube shaft, and a proximal side shaft, all of which configure the catheter shaft, are thermally fused to and integrated with each other.

Note that, the inner tube shaft is a configuration member of an inner tube forming a guide wire lumen, and the distal side shaft and the proximal side shaft are configuration members of an outer tube forming a dilating lumen through which a pressurizing medium for dilating the balloon can be circulated.

According to the above-described manufacturing method, when a process of thermally fusing and integrating the respective shafts is performed, a predetermined connection tube is connected to a proximal portion side of the inner tube shaft, thereby preventing a material from flowing into a proximal side and suppressing a possibility that a tube wall (partition wall) of a thermally fused portion may be thinned.

For example, in a manufacturing stage of the catheter shaft, if the tube wall is extremely thinned, there is a possibility that the guide wire lumen and the dilating lumen which are disposed parallel to each other across the tube wall may communicate with each other.

Therefore, after the catheter shaft is manufactured, an inspection process is performed as follows. The thermally fused tube wall is inspected to confirm a thickness of the tube wall, or to confirm that the guide wire lumen and the dilating lumen do not communicate with each other.

For example, in this inspection process, the work is carried out in order to visually confirm a thermally fused portion and a peripheral portion of the thermally fused portion in the catheter shaft.

SUMMARY

However, until now, a technique has not been sufficiently examined in which transparency (visibility from outside) of each portion of the catheter shaft is adjusted, based on a viewpoint that product quality of the catheter shaft or product quality of the balloon catheter can be improved by achieving improved accuracy of inspection results of the tube wall.

A balloon catheter is disclosed, which is capable of improving accuracy of an inspection result of a tube wall of an elongated member constituting a catheter shaft, and a method of manufacturing the elongated member for the balloon catheter which is used for the balloon catheter.

According to the present disclosure, a balloon catheter is disclosed, which includes an outer tube that includes a lumen, an inner tube that is located in the lumen of the outer tube, and that includes a guide wire lumen into which a guide wire is insertable, and a balloon that is fixed to a distal side of the inner tube and a distal side of the outer tube. A proximal portion of the inner tube is disposed so as to form a proximal opening portion, which communicates with the guide wire lumen in an intermediate portion of the outer tube. In the outer tube, at least a distal side from a proximal end of the guide wire lumen is formed of a transparent material. From a distal end toward a proximal end, the inner tube has at least a first region and a second region serving as a transparent region, which is more transparent than the first region. In an axial direction of the outer tube, the second region is disposed on a proximal side from a proximal end of the balloon, and on the distal side from the proximal end of the guide wire lumen.

According to the present disclosure, a method is disclosed of manufacturing an elongated member for a balloon catheter. The method includes an assembly process including a preparation process of preparing a transparent and hollow distal side shaft, an inner tube shaft that has a transparent region, and that forms a guide wire insertion hole for inserting a guide wire, and a hollow proximal side shaft, an inner tube shaft location process of inserting the inner tube shaft into the distal side shaft, and locating the transparent region of the inner tube shaft in a lumen portion of the distal side shaft, a proximal side shaft location process of locating the proximal side shaft so that the lumen portion of the distal side shaft and a lumen portion of the proximal side shaft communicate with each other, a process of inserting a first mandrel into the guide wire insertion hole of the inner tube shaft, and a process of inserting a second mandrel into the lumen portion of the distal side shaft and the lumen portion of the proximal side shaft, a heat-shrinkable tube location process including a heat-shrinkable tube coating process of locating a heat-shrinkable tube so as to cover the distal side shaft and the proximal side shaft, and a heat-shrinkable tube alignment process of locating a distal position of the heat-shrinkable tube on a distal side from a proximal end of the transparent region of the inner tube shaft, and a fusion process of shrinking the heat-shrinkable tube by heating the heat-shrinkable tube, and thermally fusing the distal side shaft, the inner tube shaft, and the proximal side shaft. From the distal end toward the proximal end, the inner tube shaft includes at least a first region and a second region serving as the transparent region, which is more transparent than the first region.

According to the balloon catheter of the present disclosure, a state of the tube wall in a predetermined portion of the inner tube and the outer tube can be visibly and easily confirmed via the transparent portion of the outer tube and the second region serving as the transparent region formed in the inner tube.

In this manner, accuracy of an inspection result of the tube wall can be improved, and it is possible to further improve product quality of the balloon catheter.

A balloon catheter is disclosed, the balloon catheter comprising: an outer tube that includes a lumen; an inner tube that is located in the lumen of the outer tube, and that includes a guide wire lumen into which a guide wire is insertable; a balloon that is fixed to a distal side of the inner tube and a distal side of the outer tube; a proximal portion of the inner tube being disposed to form a proximal opening portion which communicates with the guide wire lumen, between a distal end of the outer tube and a proximal end of the outer tube; the outer tube having a region that is transparent in a portion of the outer tube; the inner tube having a first region and a second region, the second region being a transparent region that is more transparent than the first region; and at least a portion of the second region overlaps the transparent region of the outer tube in an axial direction of the outer tube.

According to the method of manufacturing the elongated member for the balloon catheter of the present disclosure, the catheter shaft can be provided in which a state of the tube wall in a predetermined portion of the inner tube and the outer tube can be visibly and easily confirmed via the transparent portion of the outer tube and the second region serving as the transparent region formed in the inner tube.

Then, the balloon catheter can be manufactured using the catheter shaft, thereby improving the accuracy of the inspection result of the tube wall. Therefore, a balloon catheter can be provided whose product quality is further improved.

DESCRIPTION OF EMBODIMENTS

Hereinafter, referring to FIGS. 1 to 7B, a balloon catheter 1 according to the present embodiment and a method of manufacturing a catheter shaft 110 (corresponding to an elongated member for a balloon catheter) used as a configuration member of the balloon catheter 1 will be described.

Figure 2A:
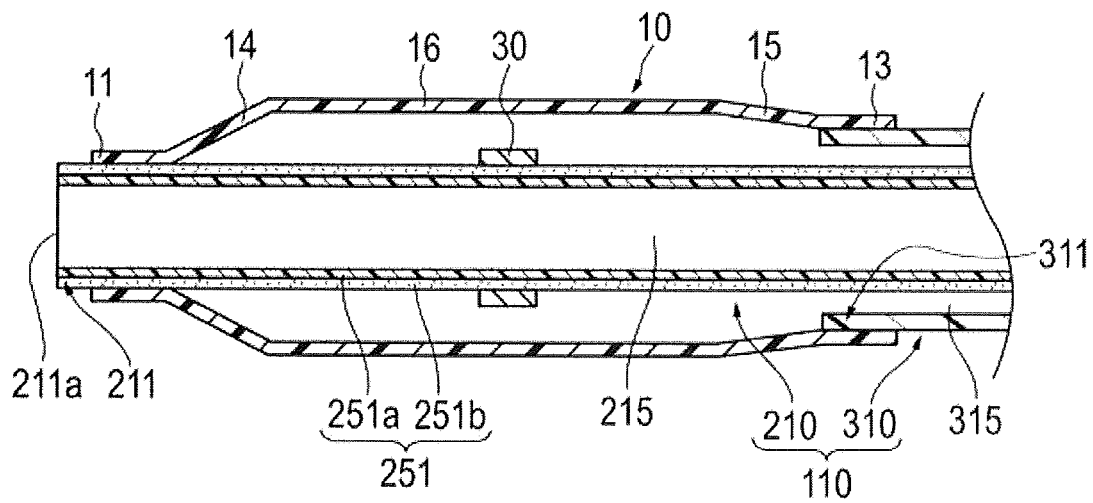
FIG. 2A is a cross-sectional view taken along an axial direction of a portion surrounded by a broken line portion IIA in FIG. 1.
Figure 2B:
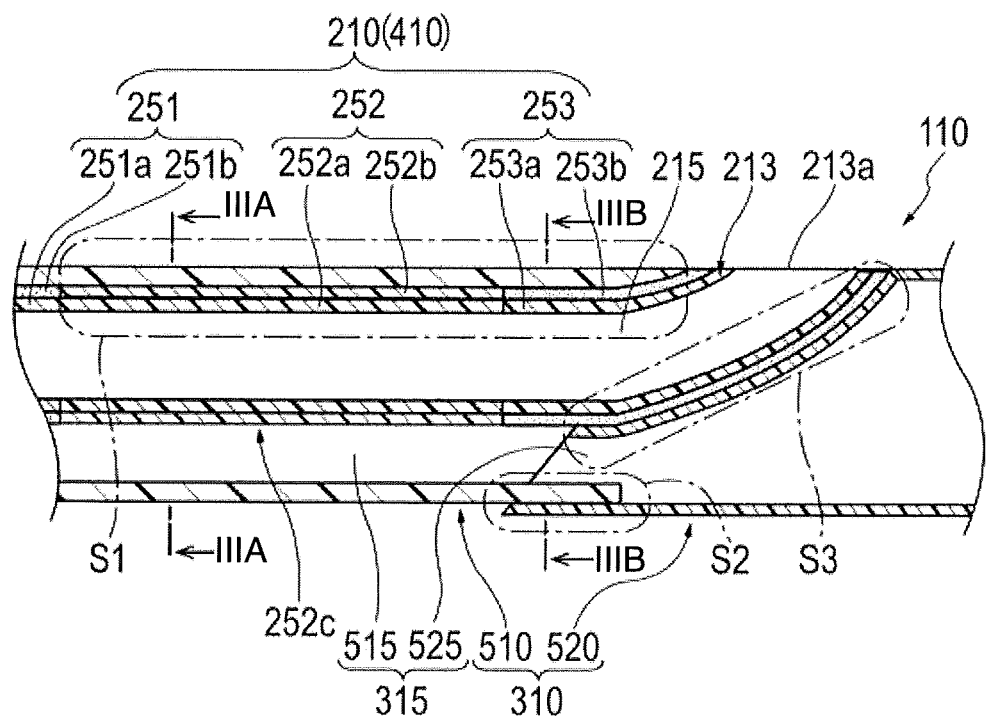
FIG. 2B is a cross-sectional view taken along the axial direction of a portion surrounded by a broken line portion IIB in FIG. 1.
Figure 3A:
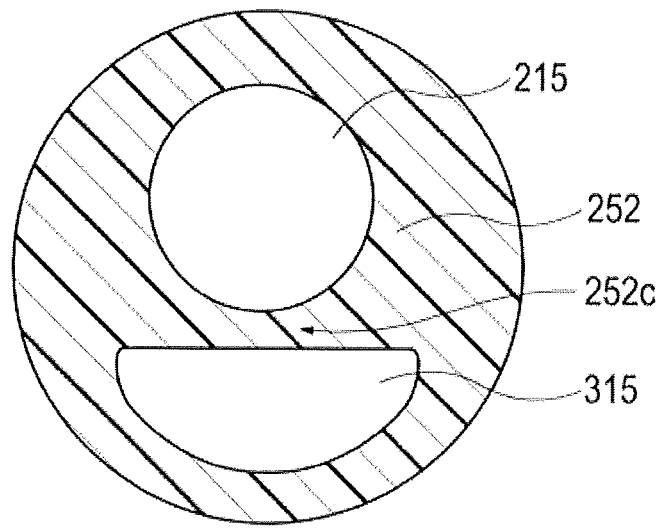
FIG. 3A is a cross-sectional view taken along line IIIA-IIIA illustrated in FIG. 2B.
Figure 3B:
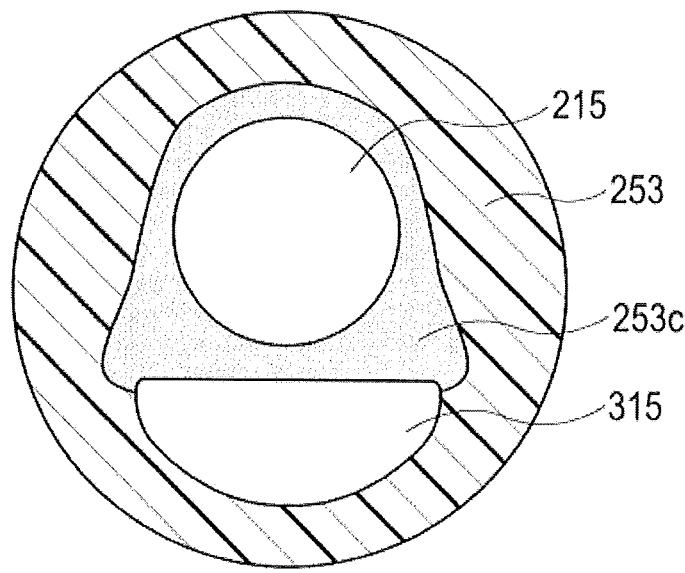
FIG. 3B is a cross-sectional view taken along line IIIB-IIIB illustrated in FIG. 2B.
Figure 4A:
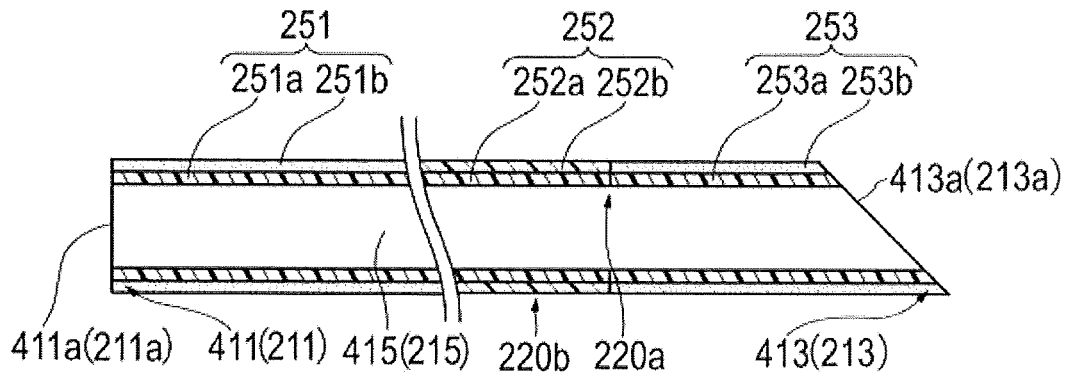
FIG. 4A is a cross-sectional view of an inner tube shaft along the axial direction.
Figure 4B:
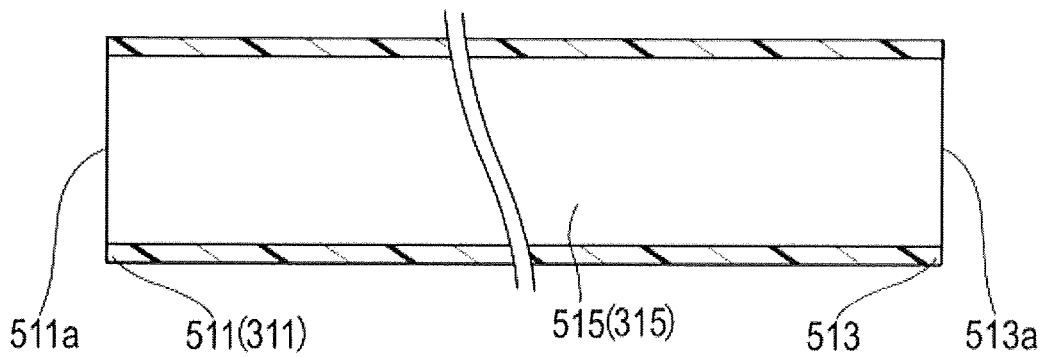
FIG. 4B is a cross-sectional view of a distal side shaft along the axial direction.

FIGS. 1 to 3B illustrate a configuration of each portion of the balloon catheter 1, and FIGS. 4A and 4B illustrate an inner tube shaft 410, a distal side shaft 510, and a proximal side shaft 520, all of which configure the catheter shaft 110.

FIGS. 5A to 7B illustrate each process of the method of manufacturing the catheter shaft 110.

Note that, dimensional ratios in the drawings are exaggerated for convenience of description, and may differ from actual ratios in some cases.

In the description herein, a side to be inserted into a living body lumen in the balloon catheter 1 and the catheter shaft 110 is referred to as a distal side, and a side which located opposite to the distal side and on which a hand-side operation is performed is referred to as a proximal side.

In addition, a direction in which the catheter shaft 110 extends is referred to as an axial direction (longitudinal direction).

Note that, a distal portion means a fixed range including a distal end (most distal end) and a periphery of the distal end (most distal end), and a proximal portion means a fixed range including a proximal end (most proximal end) and a periphery of the proximal end (most proximal end).

First, referring to FIGS. 1 to 3B, each configuration of the balloon catheter 1 will be described.

Figure 1:
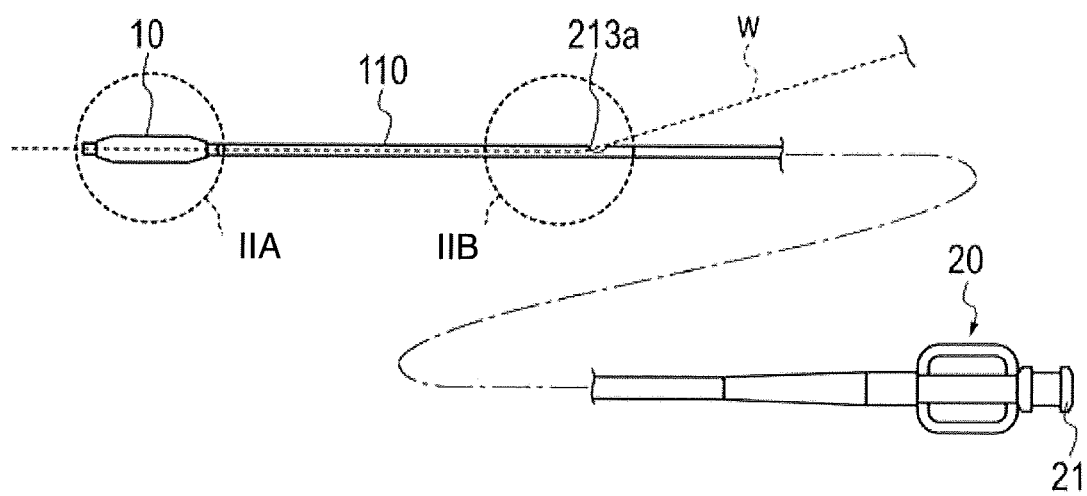
FIG. 1 is a front view of a balloon catheter according to an embodiment.

As illustrated in FIG. 1, the balloon catheter 1 has a flexible and elongated catheter shaft 110, a balloon 10 disposed on the distal portion side of the catheter shaft 110, and a hub 20 fixedly attached to the proximal portion side of the catheter shaft 110.

In accordance with an exemplary embodiment, the balloon catheter 1 is a medical device for performing treatment as follows. The elongated catheter shaft 110 is inserted into a living body lumen such as a blood vessel, and the balloon 10 disposed on the distal portion side is dilated in a lesion area (stenosed site), thereby widening the lesion area.

The catheter shaft 110 is provided with a guide wire port (proximal opening portion of an inner tube) 213a into which a guide wire w is introduced toward the distal portion side.

In other words, the balloon catheter 1 is configured to serve as a so-called rapid exchange type catheter.

As illustrated in FIG. 2A, the catheter shaft 110 has an outer tube 310 including a predetermined lumen 315, and an inner tube 210 located in the lumen 315 of the outer tube 310 and including a guide wire lumen 215 into which the guide wire w is insertable.

As will be described later, the inner tube 210 is configured to include a hollow inner tube shaft 410 (refer to FIG. 4A).

Figure 4C:
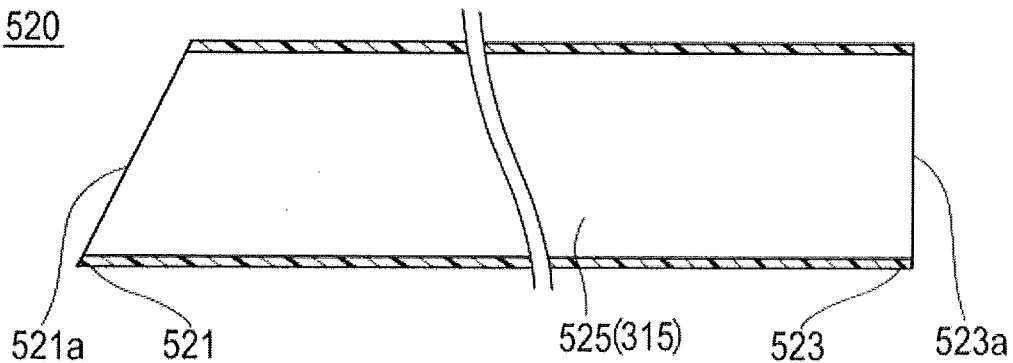
FIG. 4C is a cross-sectional view of a proximal side shaft along the axial direction.

In addition, the outer tube 310 is configured to include a hollow distal side shaft 510 and a hollow proximal side shaft 520 (refer to FIGS. 4B and 4C).

Note that, in accordance with an exemplary embodiment, a distal tip which helps prevent an inner wall of the blood vessel from being damaged when the distal end of the balloon catheter 1 comes into contact with the inner wall of the blood vessel may be attached to the distal portion of the inner tube 210.

The distal tip can be configured to include a tubular member which is more flexible than the inner tube 210.

The outer tube 310 is configured to include a hollow tube material which extends from the vicinity of a proximal portion 13 of the balloon 10 to the hub 20.

In accordance with an exemplary embodiment, the lumen 315 included in the outer tube 310 communicates with the inside of the balloon 10 on the distal side, and has a function as a dilating lumen through which a pressurizing medium is circulated into and outward from the balloon 10.

As illustrated in FIGS. 2A and 2B, the inner tube 210 includes two opening portions such as a distal opening portion 211a formed in a distal portion 211 and the proximal opening portion 213a formed in a proximal portion 213.

The guide wire lumen 215 communicates with the opening portions 211a and 213a, and extends in the axial direction.

As illustrated in FIG. 2B, the proximal portion 213 of the inner tube 210 has a shape whose proximal side is curved outward in a radial direction so that the proximal opening portion 213a communicating with the guide wire lumen 215 is located in an intermediate portion of the outer tube 310.

The proximal opening portion 213a of the inner tube 210 has a function as a guide wire port which serves as an inlet when the guide wire w is inserted into the guide wire lumen 215 and an outlet when the guide wire w is pulled out from the guide wire lumen 215.

As illustrated in FIG. 2A, the balloon 10 has an effectively dilatable portion (pressurizing portion) 16 having a straight shape which is dilated and deformed so as to widen the stenosed site formed inside the living body lumen, a distal side tapered portion 14 located on the distal side of the effectively dilatable portion 16, and a proximal side tapered portion 15 located on the proximal side of the effectively dilatable portion 16.

The balloon 10 is fixed to the distal side of the inner tube 210 and to the distal side of the outer tube 310.

More specifically, the distal portion 11 of the balloon 10 is fixed to an outer surface of the distal portion 211 of the inner tube 210, and the proximal portion 13 of the balloon 10 is fixed to an outer surface of the distal portion 311 of the outer tube 310.

The material from which the balloon 10 is fabricated is not particularly limited. However, it is possible to use polyolefin such as polyethylene, polypropylene, and ethylene-propylene copolymer, polyester such as polyethylene terephthalate, polyvinyl chloride, ethylene-vinyl acetate copolymer, cross-linked ethylene-vinyl acetate copolymer, thermoplastic resin such as polyurethane, polyamide, polyamide elastomer, polystyrene elastomer, silicone rubber, or latex rubber.

As illustrated in FIG. 1, the hub 20 includes a connection section 21 which can be air-tightly and liquid-tightly connected to a supply device (not illustrated) such as an indeflator for supplying a pressurizing medium.

For example, the connection section 21 of the hub 20 can be configured to include a known luer taper configured so that a fluid tube can be connected to the hub 20 and separated from the hub 20.

The pressurizing medium (for example, a saline solution or a contrast agent) used for dilating the balloon 10 can be caused to flow into the lumen 315 of outer tube 310 included in the catheter shaft 110 via the connection section 21 of the hub 20.

As illustrated in FIG. 2A, the inner tube 210 is provided with an X-ray contrast marker 30 indicating a central position in the axial direction of the effectively dilatable portion 16 of the balloon 10.

For example, the X-ray contrast marker 30 can be configured to include metal such as platinum, gold, silver, iridium, titanium, and tungsten, or an alloy of the metal.

Next, a configuration in the vicinity of the guide wire port 213a of the catheter shaft 110 will be described.

As illustrated in FIG. 2B, in the vicinity of the guide wire port 213a of the catheter shaft 110, the inner tube shaft 410, which constitutes the inner tube 210, and the distal side shaft 510 and the proximal side shaft 520, which constitute the outer tube 310 are thermally fused together.

The respective shafts 410, 510, and 520 are integrated with each other by means of thermal fusion.

In the description of the present embodiment, a portion where the inner tube shaft 410 and the distal side shaft 510 are thermally fused together is referred to as a first fusion portion S1, a portion where the distal side shaft 510 and the proximal side shaft 520 are thermally fused together is referred to as a second fusion portion S2, and a portion where the inner tube shaft 410 and the proximal side shaft 520 are thermally fused together is referred to as a third fusion portion S3.

Note that, the respective shafts 410, 510, and 520 are integrated with the other shaft in the thermally fused portions. Accordingly, in the actual catheter, as illustrated in FIGS. 3A and 3B, a boundary portion with the other shaft is not clearly illustrated.

However, FIG. 2B and FIGS. 4A to 7B illustrate the boundary portion of the respective shafts 410, 510, and 520 for convenience of description and understanding.

As illustrated in FIG. 4A, the inner tube shaft 410 is configured to include a tubular member that has a distal portion 411 having the distal opening portion 411a, a proximal portion 413 having a guide wire insertion hole 413a through which the guide wire w is inserted, and a hollow lumen portion 415 connected to the distal opening portion 411a and the guide wire insertion hole 413a.

As described above, the inner tube shaft 410 is a member constituting the inner tube 210 of the catheter shaft 110.

In order to facilitate understanding, the reference numeral of the inner tube 210 is marked together in the portion corresponding to each portion of the inner tube 210 in the inner tube shaft 410.

The guide wire insertion hole 413a formed in the proximal portion 413 of the inner tube shaft 410 includes a slope-shaped distal surface inclined to the proximal side.

From the distal end toward the proximal end, the inner tube shaft 410 has a first region 251, a second region 252, and a third region 253.

The second region 252 is configured to serve as a transparent region which is more transparent than the first region 251 and the third region 253.

Here, the term of being transparent does not define whether or not a material of a member itself is transparent, and means an index of visibility based on a visual sense.

In addition, the term of being more transparent means that transmittance of at least one wavelength of visible light in the one region is higher than in the other region and light is likely to be transmitted in the one region.

A transparency degree (transparency) of the second region 252 configured to serve as the transparent region is not particularly limited as long as the degree of transparency falls within a range where an inspection target portion 252c (refer to FIG. 7B) included in the second region 252 can be visually inspected.

The inner tube shaft 410 is configured so that a hollow tubular member constituting the first region 251, a hollow tubular member constituting the second region 252, and a hollow tubular member constituting the third region 253 are connected to each other.

For example, the respective tubular members constituting the inner tube shaft 410 can be connected to each other by joining respective end portions to each other using thermal fusion.

The tubular member constituting the first region 251 has an inner layer 251a and an outer layer 251b which covers the inner layer 251a.

For example, the inner layer 251a can be configured to serve as a modified polyolefin layer formed of a modified polyolefin resin.

For example, the modified polyolefin resin can include polyethylene, polypropylene, α-olefin (for example, 1-butene, 1-hexene, 4-methyl-1-pentene, 1-octene, or 1-decene) copolymer, ethylene propylene copolymer, cycloolefin polymer (for example, copolymer of cyclic olefin such as norbornene, cyclobutene, and cyclopentene), cycloolefin copolymer (for example, copolymer of cyclic olefin and chain olefin such as polyethylene, or copolymer of cyclic olefin and diene such as 1,4-hexadiene), and a material serving as a mixture of the modified polyolefin resin and having a pendant containing a polar group or a reactive group, or ethylene-vinyl acetate copolymer.

In a case of the copolymer, a structure of the copolymer is not particularly limited. It is possible to preferably use a random copolymer, an alternating copolymer, a periodic copolymer, or a block copolymer.

For example, the outer layer 251b can be configured to serve as a polyamide layer formed of a polyamide-based resin and a coloring agent.

For example, as the polyamide-based resin, those which have acid amide bond (—CO—NH—) in the main chain can be used.

In addition, as the polyamide-based resin, a polyamide elastomer resin can be used.

As the coloring agent included in the outer layer 251b, various colors such as black, red, green, blue, yellow, violet, and white depending on a desired color tone can be used.

The coloring agent can contain a pigment used for coloring the resin, and a dispersant for dispersing the pigment in the resin.

As the pigment, an inorganic pigment and an organic pigment which are known in the related art can be used.

Although not particularly limited, for example, the inorganic pigment can include carbon black, titanium oxide, barium sulfate, iron oxide (black iron oxide, yellow iron oxide, and red iron oxide), chromium oxide, ultramarine blue (ultramarine blue and ultramarine violet color), nickel titanium yellow, prussian blue, milori blue, cobalt blue, viridian, and molybdenum red.

In addition, for example, the organic pigment can include pigments of a quinacridone type (for example, quinacrid type red), a perylene type (for example, perylene red), an anthraquinone type (for example, anthraquinone type yellow), an azo type (for example, condensed azo type yellow organic pigment), and a phthalocyanine type (for example, halogenated phthalocyanine such as copper phthalocyanine and high copper chloride phthalocyanine).

The above-described pigments can be used alone or in combination of two or more types.

Note that, an intermediate layer (polyamide layer) formed of a polyamide-based resin which does not contain the coloring agent may be disposed between the inner layer 251a and the outer layer 251b.

For example, as the polyamide-based resin constituting the intermediate layer, materials that are the same as those used for the outer layer 251b can be used.

The tubular member constituting the second region 252 has an inner layer 252a and an outer layer 252b which covers the inner layer 252a.

As illustrated in FIGS. 2A and 2B, in the axial direction of the outer tube 310, the second region 252 is disposed on the proximal side from the proximal end of the balloon 10, and on the distal side of the proximal end of guide wire lumen 215.

For example, as a material of the inner layer 252a, a fluorine-based resin such as polytetrafluoroethylene, polyvinylidene fluoride, ethylene tetrafluoroethylene, and perfluoroalkoxy resin can be preferably used.

For example, as a material of the outer layer 252b, a polyolefin such as polyethylene, polypropylene, polybutene, ethylene-propylene copolymer, ethylene-vinyl acetate copolymer, ionomer, or a mixture of two or more of the materials, soft polyvinyl chloride-based resin, polyamide, polyamide elastomer, polyester, polyester elastomer, and polyurethane can be preferably used.

Note that, preferably, the second region 252 is colorless and transparent so that the inside (lumen portion) of the inner tube shaft 410 is visible from the outside of the inner tube shaft 410.

The term "transparent" as described herein does not mean that the region needs to be completely transparent, and may mean transparency ensured to such an extent that the above-described visible state is obtained.

The tubular member constituting the third region 253 has an inner layer 253a and an outer layer 253b which covers the inner layer 253a.

For example, the inner layer 253a of the third region 253 can be configured to serve as the modified polyolefin layer, similarly to the inner layer 251a of the first region 251, by using the materials of the inner layer 251a of the first region 251 described by way of example above.

In addition, for example, similarly to the outer layer 251b of the first region 251, the outer layer 253b of the third region 253 can be configured as the polyamide layer formed of a polyamide-based resin and the coloring agent.

Note that, similarly to the first region 251, an intermediate layer (polyamide layer) formed of a polyamide-based resin which does not contain the coloring agent may be disposed between the inner layer 253a and the outer layer 253b of the third region 253.

For example, in accordance with an exemplary embodiment, the third region 253 can be configured so that the content of the coloring agent per unit volume is more than that of the second region 252.

For example, if more coloring agents are contained in the third region 253 than in the second region 252, the third region 253 can be adjusted to be less transparent than the second region 252.

In accordance with the present embodiment, since the coloring agent is not contained in the second region 252, the third region 253 can contain a trace amount of the coloring agent. In this manner, the third region 253 can be adjusted to be less transparent than the second region 252.

Note that, the inner layer 251a of the first region, the inner layer 252a of the second region, and the inner layer 253a of the third region constitute the inner layer 220a of the inner tube 210.

The outer layer 251b of the first region, the outer layer 252b of the second region, and the outer layer 253b of the third region configure the outer layer 220b of the inner tube 210.

As illustrated in FIG. 4B, the distal side shaft 510 serving as a configuration member of the outer tube 310 is configured to include a tubular member that has a distal portion 511 having a distal opening portion 511a, a proximal portion 513 having a proximal opening portion 513a, and a lumen portion 515 connected to the distal opening portion 511a and the proximal opening portion 513a.

The lumen portion 515 of the distal side shaft 510, together with the lumen portion 525 of the proximal side shaft 520, forms the lumen (dilating lumen) 315 of the outer tube 310 (refer to FIG. 2B).

As illustrated in FIG. 4C, the proximal side shaft 520 of the outer tube 310 includes a tubular member that has a distal portion 521 having a distal opening portion 521a, a proximal portion 523 having a proximal opening portion 523a, and a lumen portion 525 connected to the distal opening portion 521a and the proximal opening portion 523a.

The distal opening portion 521a formed in the distal portion 521 of the proximal side shaft 520 includes a slope-shaped distal surface inclined to the distal side.

For example, as a material of the distal side shaft 510 and the proximal side shaft 520, a polyolefin such as polyethylene, polypropylene, polybutene, ethylene-propylene copolymer, ethylene-vinyl acetate copolymer, and ionomer, or a mixture of two or more of the materials, or fluororesin such as soft polyvinyl chloride-based resin, polyamide, polyamide elastomer, polyester, polyester elastomer, polyurethane, and polytetrafluoroethylene can be preferably used.

For example, the proximal side shaft 520 may have a configuration in which a plurality of shafts are joined to each other in the axial direction.

In this case, the proximal portion of the proximal side shaft 520 can be formed of a metal material such as stainless steel and aluminum, for example. The distal portion of the proximal side shaft 520 can be formed of the above-described resin material, for example.

In addition, a shaft provided with a reinforcement body for adjusting rigidity of the catheter shaft 110 so as to help prevent kinking may be connected to the proximal side of the proximal side shaft 520.

In accordance with an exemplary embodiment, the distal side shaft 510 and the proximal side shaft 520 are formed of a transparent material.

Therefore, the outer tube 310 can be configured so that the distal side portion is more transparent than the proximal end of the guide wire lumen 215.

The transparency of the respective shafts 510 and 520 can be appropriately adjusted to such an extent that the inner tube 210 located inside the outer tube 310 is visible from the outside of the outer tube 310.

Next, an inspection target portion (non-fused portion) 252c of the catheter shaft 110 will be described.

As illustrated in FIGS. 2B, 3A, and 3B, the guide wire lumen 215 formed in the inner tube 210 and the lumen 315 formed in the outer tube 310 are disposed parallel to each other along the axial direction of the catheter shaft 110.

In the inner tube 210, the fusion portions S1 and S2 thermally fused to the distal side shaft 510 or the proximal side shaft 520 are integrated with each other by adjacent tube walls overlapping each other. Accordingly, after thermal fusion, the thickness of the fusions portions S1 and S2 increases.

In accordance with an exemplary embodiment, in the inner tube 210, the non-fused portion 252c is not thermally fused to the distal side shaft 510 or the proximal side shaft 520. Accordingly, the thickness does not increase even after the thermal fusion.

Figure 7A:
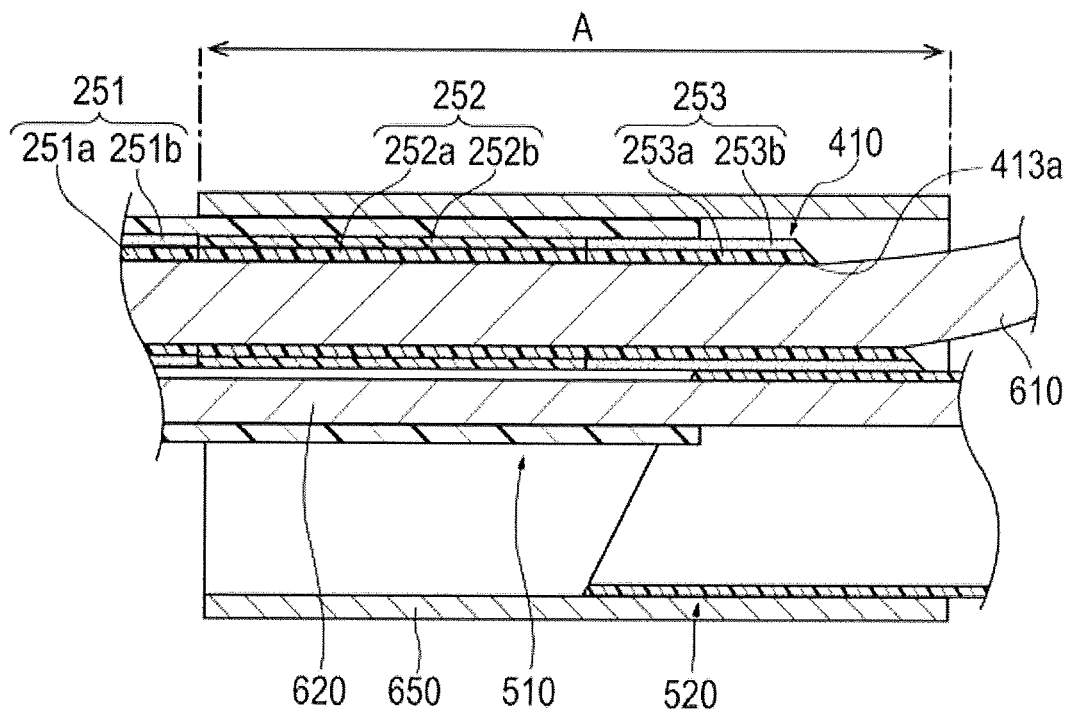
FIGS. 7A and 7B are views for describing a method of manufacturing an elongated member for a balloon catheter according to the embodiment, and are views illustrating each state of a heat-shrinkable tube location process and a fusion process.
Figure 7B:
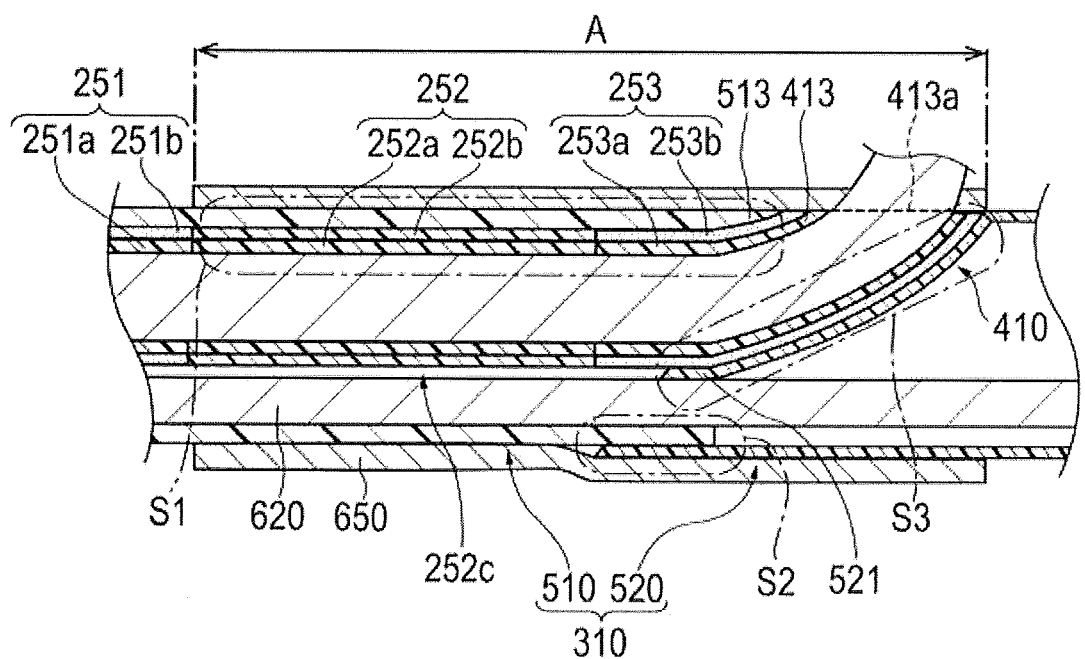

In addition, when the thermal fusion is performed, heat is applied to the non-fused portion 252c in a state of being interposed between two mandrels 610 and 620 (refer to FIGS. 7A and 7B). Accordingly, after the thermal fusion, the thickness of the non-fused portion 252c may become thinner than that before the thermal fusion.

If the thickness of the non-fused portion 252c becomes extremely thinner, there is a possibility that the guide wire lumen 215 formed in the inner tube 210 and the lumen 315 formed in the outer tube 310 may communicate with each other.

Therefore, after the thermal fusion, the non-fused portion 252c is set as an inspection target portion. In this manner, an inspection process is performed in order to confirm whether or not the thickness of the non-fused portion 252c is formed to have a sufficient thickness, and whether or not the guide wire lumen 215 and the lumen 315 communicate with each other.

For example, the above-described inspection process is performed by visibly recognizing the inside of the catheter shaft 110 from outside.

For example, the inside can be visibly recognized as follows. An enlarged image in the vicinity of the inspection target portion 252c is projected using a predetermined inspection tool, and the image is viewed so as to look into the depth in the thickness direction (for example, a direction orthogonal to the paper surface of FIGS. 2A and 2B) of the catheter shaft 110.

Therefore, if the second region 252 including the inspection target portion 252c is less transparent, the inside of the catheter shaft 110 cannot be identified, thereby causing poor accuracy of the inspection result.

For purposes of convenience when the balloon catheter 1 is used, the first region 251 located on the distal side may be less transparent to some extent than the second region 252.

In addition, the third region 253 located on the proximal side from the second region 252 may be less transparent than the second region 252, from a viewpoint that a position of the guide wire port 213a can be relatively easily recognized when the balloon catheter 1 is used, and that a position of the guide wire port 213a can be recognized when the catheter shaft 110 is manufactured.

Therefore, the catheter shaft 110 according to the present embodiment is formed so that the second region 252 of the inner tube shaft 410 is more transparent than the first region 251 and the third region 253.

Note that, a relationship relating to which is more transparent is not particularly limited between the first region 251 and the third region 253. However, for example, the third region 253 may be less transparent than the first region 251.

If the third region 253 is formed in this way, the position of the guide wire port 213a can be rather easily recognized. Therefore, a medical procedure can be more smoothly performed, and a manufacturing process is further facilitated.

The thickness of the tube wall in a portion having the inspection target portion 252c is thinner than the thickness of the first region 251 which is less influenced by heat during the thermal fusion.

In accordance with an exemplary embodiment, the thickness of the tube wall in the portion having the inspection target portion 252c can be thinner than the thickness of the distal portion 211 of the inner tube 210 which is extremely less influenced by the heat during the thermal fusion.

In accordance with an exemplary embodiment, the distal portion 211 of the inner tube 210 which is less influenced by the heat during the thermal fusion is the distal end (most distal end) of the inner tube 210 in a case where the distal tip is not attached to the inner tube 210, and is the distal side of the inner tube 210 and a portion on the proximal side from the proximal end of the distal tip in a case where the distal tip is attached to the inner tube 210.

In the present embodiment, the second region 252 serving as the transparent region which is more transparent is disposed in a portion where the thickness of the tube wall becomes thinner than that of the first region 251 of the inner tube 210. In addition, the second region 252 is a portion that includes the inspection target portion 252c.

As illustrated in FIG. 3B, if the thermal fusion is performed, the outer layer 253b of the third region 253 melts and spreads to the periphery.

A portion colored by the melted outer layer 253b forms a colored portion 253c of the catheter shaft 110.

Since the coloring agent is contained in the outer layer 253b, the outer layer 253b spreads outward of the tube wall, thereby forming the colored portion 253c.

Therefore, at a stage of manufacturing the catheter shaft 110, the colored portion 253c can be formed over a relatively wide range of the third region 253, and the third region 253 can be more easily identified.

Next, referring to FIGS. 5A to 7B, a method of manufacturing the catheter shaft 110 will be described.

Here, each process performed until the inner tube shaft 410, the distal side shaft 510, and the proximal side shaft 520 are integrated with each other in the vicinity of the guide wire port 213a will be described.

First, a preparation process is performed.

The inner tube shaft 410, the distal side shaft 510, and the proximal side shaft 520, which form the catheter shaft 110, are prepared (refer to FIGS. 4A-4C).

Next, an assembly process is performed.

Figure 5A:
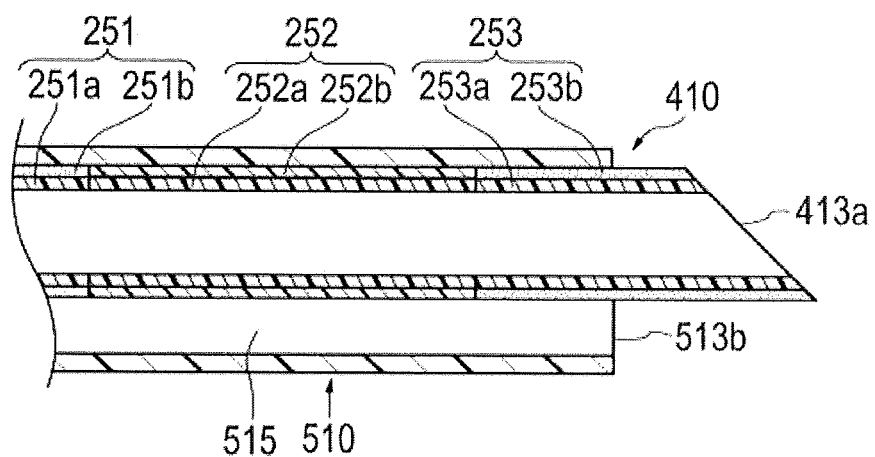
FIGS. 5A and 5B are views for describing a method of manufacturing an elongated member for a balloon catheter according to the embodiment, and are views illustrating each state of a preparation process and an assembly process.

As illustrated in FIG. 5A, the inner tube shaft 410 is inserted into the distal side shaft 510, and the second region (transparent region) 252 of the inner tube shaft 410 is located in the lumen portion 515 of the distal side shaft 510 (inner tube shaft location process).

Figure 5B:
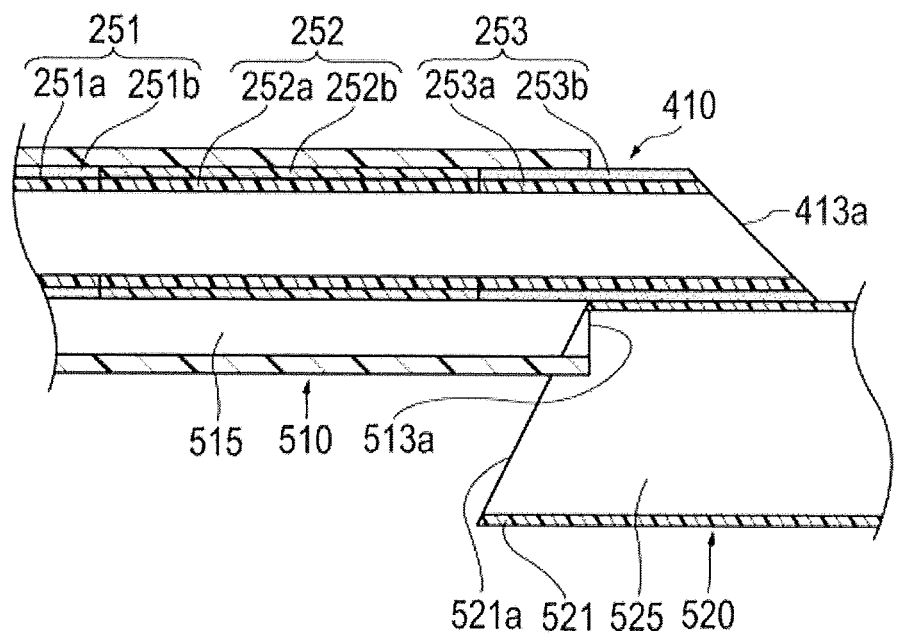

As illustrated in FIG. 5B, the proximal side shaft 520 is located so that the lumen portion 515 of the distal side shaft 510 and the lumen portion 525 of the proximal side shaft 520 communicate with each other (proximal side shaft location process).

In this case, a portion of the distal portion 521 of the proximal side shaft 520 is inserted into the lumen portion 515 of the distal side shaft 510.

Note that, it is preferable that the distal end of the proximal side shaft 520 is located on the proximal side from the proximal end of the second region 252 of the inner tube shaft 410.

According to this configuration, the inspection target portion 252c of the catheter shaft 110 can be formed to be long in the axial direction.

Figure 6A:
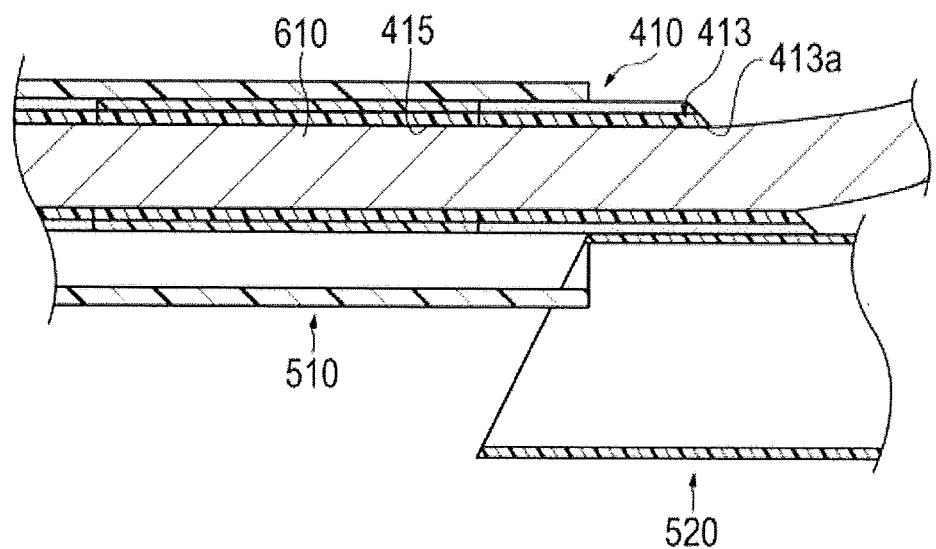
FIGS. 6A and 6B are views for describing a method of manufacturing an elongated member for a balloon catheter according to the embodiment, and are views illustrating a state of an assembly process.

As illustrated in FIG. 6A, the first mandrel (first core bar) 610 is inserted into the guide wire insertion hole 413a of the inner tube shaft 410.

The first mandrel 610 is inserted into the lumen portion 415 of the inner tube shaft 410.

As the first mandrel 610, in accordance with an exemplary embodiment, for example, it is possible to use those which have a cross-sectional shape corresponding to a cross-sectional shape of the guide wire lumen 215 illustrated in FIG. 3A.

Figure 6B:
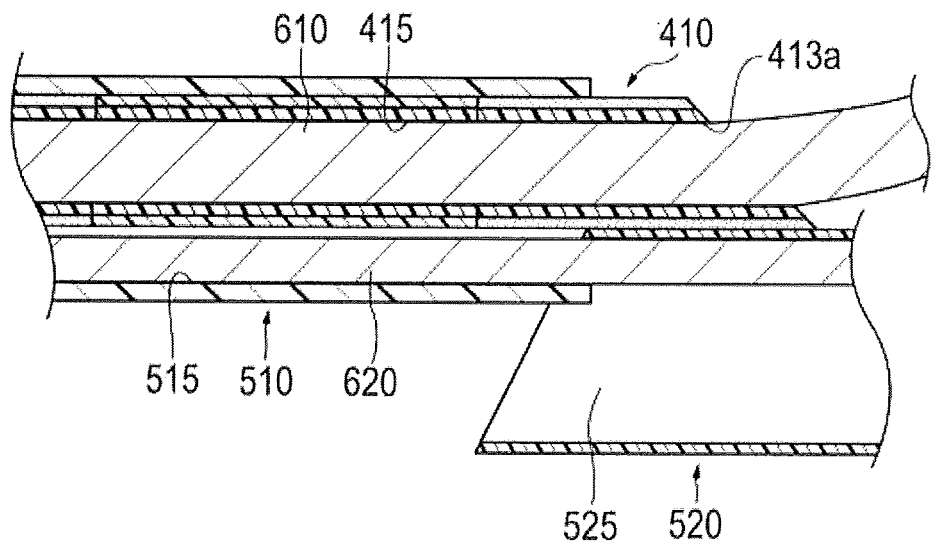

As illustrated in FIG. 6B, the second mandrel (second core bar) 620 is inserted into the lumen portion 515 of the distal side shaft 510 and the lumen portion 525 of the proximal side shaft 520.

As the second mandrel 620, for example, it is possible to use those which have a cross-sectional shape corresponding to a cross-sectional shape of the dilating lumen 315 illustrated in FIG. 3A.

Note that, the inner tube shaft location process and the proximal side shaft location process can be switched therebetween in the order of processes.

Similarly, the process of inserting the first mandrel 610 and the process of inserting the second mandrel 620 can be switched therebetween in the order of processes.

Next, a heat-shrinkable tube location process is performed.

As illustrated in FIG. 7A, the heat-shrinkable tube 650 is located so as to cover the distal side shaft 510 and the proximal side shaft 520 (heat-shrinkable tube coating process).

For example, as the heat-shrinkable tube 650, a hollow cylindrical member configured to include polyolefin can be used.

In accordance with an exemplary embodiment, the heat-shrinkable tube 650 shrinks if the heat-shrinkable tube 650 is heated, and is deformed so that the diameter after being heated is smaller than the diameter before being heated.

Therefore, in a state where the heat-shrinkable tube 650 is attached to the outer periphery of the distal side shaft 510 and the proximal side shaft 520, the heat-shrinkable tube 650 is heated, thereby applying the pressurizing force from the outside toward the inside of the distal side shaft 510, the inner tube shaft 410, and the proximal side shaft 520.

As illustrated in FIG. 7A, the distal position of the heat-shrinkable tube 650 is located on the distal side from the proximal end of the second region 252 of the inner tube shaft 410 (heat-shrinkable tube alignment process).

In this case, the proximal position of the heat-shrinkable tube 650 is located on the proximal side from the proximal end of the second region 252.

Preferably, the proximal position of the heat-shrinkable tube 650 is located on the proximal side from the proximal end of the third region 253.

For example, the distal position of the heat-shrinkable tube 650 is located in the vicinity of the distal end of the second region 252, the proximal position of the heat-shrinkable tube 650 is located in the vicinity of the proximal end of the third region 253.

In accordance with an exemplary embodiment, a region A in FIG. 7A indicates a range where the heat-shrinkable tube 650 is located.

Next, a fusion process is performed.

As illustrated in FIG. 7B, heat is applied to the heat-shrinkable tube 650 so as to shrink, and the distal side shaft 510, the inner tube shaft 410, and the proximal side shaft 520 are thermally fused together.

In this manner, the distal side shaft 510 and the second region 252 of the inner tube shaft 410 are fused and integrated with each other.

In addition, the proximal portion 513 of the distal side shaft 510 and the third region 253 of the inner tube shaft 410 are fused and integrated with each other.

In addition, the distal portion 521 of the proximal side shaft 520 and the third region 253 of the inner tube shaft 410 are fused and integrated with each other.

In addition, the proximal portion 513 of the distal side shaft 510 and the distal portion 521 of the proximal side shaft 520 are fused and integrated with each other.

After the fusion process is performed, the heat-shrinkable tube 650 is removed, and the first mandrel 610 and the second mandrel 620 are detached. In this manner, as illustrated in FIG. 2B, the catheter shaft 110 integrated via the respective fusion portions S1, S2, and S3 can be manufactured.

The balloon 10 and the hub 20 are attached to the catheter shaft 110. In this manner, it is possible to manufacture the balloon catheter 1.

As described above, the balloon catheter 1 according to the present embodiment includes the outer tube 310 including the lumen 315, the inner tube 210 located in the lumen 315 of the outer tube 310 and including the guide wire lumen 215 into which the guide wire w is insertable, and the balloon 10 fixed to the distal side of the inner tube 210 and the distal side of the outer tube 310.

The proximal portion 213 of the inner tube 210 is disposed so as to form the guide wire port 213a which communicates with the guide wire lumen 215 in the intermediate portion of the outer tube 310. In the outer tube 310, at least the distal side from the proximal end of the guide wire lumen 215 is formed of the transparent material.

From the distal end toward the proximal end, the inner tube 210 has at least the first region 251 and the second region 252 serving as the transparent region which is more transparent than the first region 251.

Then, in the axial direction of the outer tube 310, the second region 252 is disposed on the proximal side from the proximal end of the balloon 10, and on the distal side from the proximal end of the guide wire lumen 215.

According to the balloon catheter 1 configured as described above, it is possible to visibly and easily confirm a state of the tube wall in the inspection target portion 252c of the catheter shaft 110 via the transparent portion of the outer tube 310 and the second region 252 serving as the transparent region formed in the inner tube 210.

In this manner, the accuracy of the inspection result of the tube wall can be improved, and the product quality of the balloon catheter 1 can be further improved.

In addition, the second region 252 is disposed in at least a portion where the thickness of the tube wall is formed to be thinner than the distal portion 211 of the inner tube 210. Accordingly, in the portion where the thickness of the tube wall is thinned, the thickness of the tube wall and a communication state between the guide wire lumen 215 and the dilating lumen 315 can be inspected.

In addition, the inner tube 210 has the third region 253 which is formed on the proximal side from the second region 252 and which is less transparent than the second region 252. Accordingly, the visibility of the proximal portion 213 of the inner tube 210 can be improved. Therefore, the position of the guide wire port 213a formed in the proximal end of the inner tube 210 can be relatively easily recognized.

As a result, a medical procedure using the balloon catheter 1 can be smoothly performed.

Furthermore, the position of the guide wire port 213a can be easily recognized when the catheter shaft 110 is manufactured. Therefore, the manufacturing work can be carried out more efficiently.

In addition, the inner tube 210 includes the inner layer 220a and the outer layer 220b which covers the inner layer 220a, and the outer layer 253b in the portion constituting the third region 253 includes more coloring agents than the outer layer 252b in the portion constituting the second region 252. Therefore, the third region 253 can be easily identified.

In this manner, the convenience of the balloon catheter 1 and the efficiency of the manufacturing work can be further improved.

In addition, the method of manufacturing the catheter shaft 110 according to the present embodiment has the assembly process including the preparation process of preparing the transparent and hollow distal side shaft 510, the inner tube shaft 410 that has the second region (transparent region) 252, and that forms the guide wire port (guide wire insertion hole) 413a for inserting the guide wire w, and the hollow proximal side shaft 520, the inner tube shaft location process of inserting the inner tube shaft 410 into the distal side shaft 510, and locating the second region 252 of the inner tube shaft 410 in the lumen portion 515 of the distal side shaft 510, the proximal side shaft location process of locating the proximal side shaft 520 so that the lumen portion 515 of the distal side shaft 510 and the lumen portion 525 of the proximal side shaft 520 communicate with each other, the process of inserting the first mandrel 610 into the guide wire insertion hole 413a of the inner tube shaft 410, and the process of inserting the second mandrel 620 into the lumen portion 515 of the distal side shaft 510 and the lumen portion 525 of the proximal side shaft 520, the heat-shrinkable tube location process including the heat-shrinkable tube coating process of locating the heat-shrinkable tube 650 so as to cover the distal side shaft 510 and the proximal side shaft 520, and the heat-shrinkable tube alignment process of locating the distal position of the heat-shrinkable tube 650 on the distal side from the proximal end of the second region 252 of the inner tube shaft 410, and the fusion process of shrinking the heat-shrinkable tube 650 by heating the heat-shrinkable tube 650, and thermally fusing the distal side shaft 510, the inner tube shaft 410, and the proximal side shaft 520.

Then, from the distal end toward the proximal end, the inner tube shaft 410 has at least the first region 251 and the second region 252 serving as the transparent region which is more transparent than the first region 251.

According to the above-described manufacturing method, it is possible to provide the catheter shaft 110 which can visibly and easily confirm a state of the tube wall in the inspection target portion 252c of the catheter shaft 110 via the transparent portion of the outer tube 310 and the second region 252 serving as the transparent region formed in the inner tube 210.

Then, the balloon catheter 1 is manufactured using the catheter shaft 110, thereby improving the accuracy of the inspection result of the tube wall. Accordingly, it is possible to provide the balloon catheter 1 whose product quality is further improved.

In the addition, in the heat-shrinkable tube alignment process, the proximal position of the heat-shrinkable tube 650 is located on the proximal side from the proximal end of the second region 252. In the fusion process, the distal side shaft 510 and the second region 252 of the inner tube shaft 410 are fused together. In this manner, the second region 252 can be disposed so as to include the portion where the thickness of the tube wall is formed to be thinner than the distal end of the inner tube 210 after the thermal fusion.

Therefore, in the portion where the thickness of the tube wall is thinned, it is possible to preferably inspect the thickness of the tube wall and a communication state between the guide wire lumen 215 and the dilating lumen 315.

In addition, the inner tube shaft 410 further includes the third region 253 which is formed on the proximal side from the second region 252 and which is less transparent than the second region 252. In the fusion process, the proximal portion 513 of the distal side shaft 510 and the third region 253 of the inner tube shaft 410 are fused together, and the distal portion 511 of the proximal side shaft 520 and the third region 253 of the inner tube shaft 410 are further fused together, thereby improving the visibility of the proximal portion 213 of the inner tube 210. Therefore, it is possible to easily recognize the position of the guide wire port 213a formed in the proximal end of the inner tube 210.

As a result, a medical procedure using the balloon catheter 1 can be smoothly performed, and the position of the guide wire port 213a can be easily recognized when the catheter shaft 110 is manufactured. Therefore, the manufacturing work can be carried out more efficiently.

In addition, the inner tube 210 includes the inner layer 220a and the outer layer 220b which covers the inner layer 220a, and the outer layer 253b in the portion constituting the third region 253 includes the more coloring agent than the outer layer 252b in the portion constituting the second region 252. In this manner, the third region 253 can be relatively easily identified. Therefore, the convenience of the balloon catheter 1 and the efficiency of the manufacturing work can be further improved.

Hitherto, the balloon catheter and the method of manufacturing the elongated member for the balloon catheter according to the present disclosure have been described with reference to the embodiment. However, the present disclosure is not limited to only the content described in the embodiment, and can be appropriately modified, based on the description of appended claims.

Each shape of the inner tube (the inner tube shaft) and the outer tube (the distal side shaft and the proximal side shaft) which constitute the catheter shaft is not limited to the illustrated shape.

For example, a cross-sectional shape of each shaft is not limited to a circular shape, and may be a polygonal shape or an elliptical shape.

In addition, an example has been described in which the proximal surface of the inner tube shaft and the distal surface of the proximal side shaft are formed as a slope. However, these surfaces may not be the slope, and may be formed as a plane orthogonal to the axial direction.

In addition, a slit extending in the axial direction may be formed on the distal surface of the distal side shaft or on the distal surface of the proximal side shaft, and the thermal fusion may be performed in a state where the tube wall of each shaft is located while being inserted into the slit.

In addition, the distal position and the proximal position of the heat-shrinkable tube when the thermal fusion process is performed using the heat-shrinkable tube may be located at any position as long as the distal side shaft, the inner tube shaft, and the proximal side shaft can be thermally fused together. The position is not limited to the illustrated position.

In addition, an example has been described in which the inner tube (inner tube shaft) includes the first region, the second region, and the third region. However, the inner tube (inner tube shaft) may include at least the first region and the second region serving as the transparent region which is more transparent than the first region, and may not have the third region. In addition, the inner tube may include other transparent regions different from the first region, the second region, and the third region.

In addition, the balloon catheter is not limited to a use for widening the lesion area (stenosed site), and may be configured to serve as a balloon catheter for stent delivery, for example.

In addition, a structure of each portion or location of a member of the balloon catheter described in the embodiment can be appropriately modified. It is possible to omit the use of additional members described with reference to the drawings, and it is also possible to appropriately use other additional members.

Similarly, it is also possible to appropriately modify each process relating to the method of manufacturing the elongated member for the balloon catheter or the equipment used for the manufacturing.

The detailed description above describes a balloon catheter serving as a medical device, and a manufacturing method of an elongated member for a balloon catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter, the balloon catheter comprising:
an outer tube that includes a lumen;
an inner tube that is located in the lumen of the outer tube and includes a guide wire lumen configured to receive a guide wire;
a balloon fixed to a distal side of the inner tube and a distal side of the outer tube;
a proximal portion of the inner tube including a proximal opening portion which communicates with the guide wire lumen in an intermediate portion of the outer tube;
a portion of the outer tube distal from a proximal end of the guide wire lumen being formed of a transparent material;
the inner tube, from a distal end toward a proximal end, including at least a first region and a second region, the second region being a transparent region that is more transparent than the first region; and
in an axial direction of the outer tube, the second region being disposed on a proximal side from a proximal end of the balloon and being disposed on a distal side from the proximal end of the guide wire lumen, and wherein the second region includes at least a portion of the inner tube whose tube wall is formed to be thinner than that of a distal portion of the inner tube.

2. The balloon catheter according to claim 1,
wherein the inner tube further has a third region which is formed on a proximal side from the second region, the third region being less transparent than the second region.

3. The balloon catheter according to claim 2,
wherein the inner tube includes an inner layer and an outer layer which covers the inner layer; and wherein the outer layer in a portion of the third region includes coloring agents, the third region having more coloring agents than the outer layer in a portion of the second region.

4. The balloon catheter according to claim 3, wherein the second region does not contain any coloring agents.

5. The balloon catheter according to claim 1, wherein the inner tube further has a third region which is formed on a proximal side from the second region, the third region being less transparent than the second region.

6. A balloon catheter, the balloon catheter comprising:
an outer tube having a distal portion, a proximal portion, and an intermediate portion between the proximal portion and distal portion, the outer tube having a lumen;
an inner tube that is located in the lumen of the outer tube and includes a guide wire lumen configured to receive a guide wire;
a balloon fixed to a distal side of the inner tube and a distal side of the outer tube;
a proximal portion of the inner tube including a proximal opening portion which communicates with the guide wire lumen;
the proximal opening portion located on an outer surface of the intermediate portion of the outer tube;
the intermediate portion of the outer tube around the proximal opening portion formed of a transparent material, the intermediate portion being more transparent than the proximal portion of the outer tube; and
the proximal opening portion of the inner tube being a transparent region.

7. The balloon catheter according to claim 6, wherein the inner tube includes a first region and a second region, the second region being a transparent region that is more transparent than the first region; and the second region includes at least a portion of the inner tube whose tube wall is formed to be thinner than that of a distal portion of the inner tube.

8. The balloon catheter according to claim 7, wherein the inner tube further has a third region which is formed on a proximal side from the second region, the third region being less transparent than the second region.

9. The balloon catheter according to claim 8, wherein the inner tube includes an inner layer and an outer layer which covers the inner layer, and
wherein the outer layer in a portion of the third region includes coloring agents, the third region having more coloring agents than the outer layer in a portion of the second region.

10. The balloon catheter according to claim 9, wherein the second region does not contain any coloring agents.

11. The balloon catheter according to claim 6, wherein the inner tube includes a first region and a second region, and the inner tube further includes a third region which is formed on a proximal side from the second region, the third region being less transparent than the second region.

12. A method of manufacturing the balloon catheter according to claim 1, the method comprising:
preparing a transparent and hollow distal side shaft of the outer tube, the inner tube having a guide wire insertion hole configured to receive the guide wire, and a hollow proximal side shaft of the outer tube, the distal side shaft including a lumen and the proximal side shaft including a lumen;
inserting the inner tube into the distal side shaft, and locating the transparent region of the inner tube in the lumen of the distal side shaft;
locating the proximal side shaft so that the lumen of the distal side shaft and the lumen of the proximal side shaft communicate with each other;
inserting a first mandrel into the guide wire insertion hole of the inner tube shaft;
inserting a second mandrel into the lumen of the distal side shaft and the lumen of the proximal side shaft;
locating a heat-shrinkable tube to cover the distal side shaft and the proximal side shaft;
locating a distal position of the heat-shrinkable tube on a distal side from a proximal end of the transparent region of the inner tube; and
shrinking the heat-shrinkable tube by heating the heat-shrinkable tube, and thermally fusing the distal side shaft, the inner tube shaft, and the proximal side shaft; and
fixing the balloon to the distal side of the inner tube and the distal side of the outer tube.

13. The method of manufacturing the balloon catheter according to claim 12, further comprising:
locating a proximal position of the heat-shrinkable tube on a proximal side from a proximal end of the second region; and
fusing the distal side shaft and the second region of the inner tube shaft together.

14. The method of manufacturing the balloon catheter according to claim 13, wherein the inner tube further includes a third region on the proximal side from the second region, and the third region being less transparent than the second region, the method further comprising:
fusing a proximal portion of the distal side shaft and the third region of the inner tube together; and
fusing a distal portion of the proximal side shaft and the third region of the inner tube together.

15. The method of manufacturing the balloon catheter according to claim 12,
wherein the inner tube includes an inner layer and an outer layer which covers the inner layer, and
wherein the outer layer in a portion of the third region includes coloring agents, the third region having more coloring agents than the outer layer in a portion of the second region.

* * * * *